United States Patent [19]

Tang et al.

[11] Patent Number: 4,944,944

[45] Date of Patent: Jul. 31, 1990

[54] DIETARY COMPOSITIONS AND METHODS USING BILE SALT-ACTIVATED LIPASE

[75] Inventors: Jordan J. N. Tang; Chi-Sun Wang, both of Oklahoma City, Okla.

[73] Assignee: Oklahoma Medical Research Foundation, Oklahoma City, Okla.

[21] Appl. No.: 122,410

[22] Filed: Nov. 19, 1987

[51] Int. Cl.$^5$ .................. A61K 37/54; A23C 9/00; A23L 2/38

[52] U.S. Cl. .................. 424/94.6; 424/535; 426/2; 426/580; 426/588; 426/801

[58] Field of Search .............. 424/94.6, 95; 426/580, 426/588, 801, 2

[56] References Cited

FOREIGN PATENT DOCUMENTS 662815 5/1963 Canada .................. 424/94.6

OTHER PUBLICATIONS

Hernell, "Human Milk Lipases", *Europ. J. Clin. Invest.* 5, 267–272 (1975).

S. Williamson, et al., Arch. Dis. Child., 53, 555–563, 1978, "Effect of Heat Treatment of Human Milk on Absorption of Nitrogen, Fat, Sodium, Calcium, and Phosphorus by Preterm Infants".

C. Wang, J. Biol. Chem., 256:10198–10202, 1981, "Human Milk Bile Salt-Activated Lipase".

B. Alemi, et al., Pediatrics, 68:484–489, 1981, "Fat Digestion in Very Low-Birth-Weight Infants: Effect of Addition of Human Milk to Low-Birth-Weight Formula".

C. Wang, et al., Anal. Biochem., 133:457–461, 1983, "Purification of Human Milk Bile Salt-Activated Lipase".

C. Wang, et al., Biochim. Biophys. Acta, 754:142–149, 1983, "Kinetic Properties of Human Pancreatic Carboxylesterase".

C. Wang, ed., Fat Adsorption, vol. 1, CRC Press, 1986, Chapter 3, "Hydrolysis of Dietary Glycerides and Phosphoglycerides: Fatty Acid and Positional Specificity of Lipases and Phospholipases".

C. Wang, et al., J. Lipid Res., 26:824–830, 1985, "Kinetic Properties of Human Milk Bile Salt-Activated Lipase: Studies Using Long Chain Triacylglycerol as Substrate".

L. Freed, et al., Biochim. Biophys. Acta, 878:209–215, 1986, "Bile Salt-Stimulated Lipase in Non-Primate Milk: Longitudinal Variation and Lipase Characteristics in Cat and Dog Milk".

*Primary Examiner*—Jacqueline Stone
*Attorney, Agent, or Firm*—Kilpatrick & Cody

[57] ABSTRACT

Dietary compositions, especially cow's milk-based infant formulas, are fortified with bile salt-activated lipase. Methods are provided for feeding newborn and premature infants which include administration of bile salt-activated lipase to increase fat digestion and therefore growth rate. Similarly, a method is provided to treat subjects for inadequate pancreatic enzyme production by administration of bile salt-activated lipase in conjunction with ingestion of fats.

23 Claims, No Drawings

DIETARY COMPOSITIONS AND METHODS USING BILE SALT-ACTIVATED LIPASE

Field of the Invention

The present invention relates to dietary compositions in general and in particular to dietary compositions and methods using bile salt-activated lipase.

SUMMARY OF THE INVENTION

The present invention is directed to a dietary composition which comprises a nutritional base from a first source containing fats and being poor in bile salt-activated lipase. The composition further comprises an effective amount of bile salt-activated lipase derived from a second source. The present invention also comprises an infant formula for a first animal species which comprises milk from a second animal species and an effective amount of bile salt-activated lipase derived from a species other than the second animal species.

The present invention further comprises a method for fortifying cow's milk. An effective amount of bile salt-activated lipase is added thereto. The lipase is derived from an animal species other than a cow. According to the present invention other fat-containing infant formulas which are poor in bile salt-activated lipase may be similarly fortified by adding an effective amount of bile salt-activated lipase.

The present invention further comprises a method for treating a subject for inadequate pancreatic production of bile salt-activated lipase. Bile salt-activated lipase is administered to the subject in conjunction with the ingestion of fats and in an amount sufficient to improve the subject's digestion of the fats.

Finally, the present invention includes a method for feeding an infant. A fat-containing dietary base is administered to the infant. In conjunction therewith, bile salt-activated lipase is administered to the infant in an amount sufficient to improve the infant's digestion of the fats in the base.

DESCRIPTION OF THE PREFERRED EMBODIMENTS

In warm-blooded animals, the proper digestion of fat requires a class of digestive enzymes called lipases. Lipases occur in many forms and are produced by several of the digestive organs, including the pancreas, stomach and small intestines. The present invention concerns a subclass of lipases called bile salt-activated lipases, so named because they are secreted in an inactive form and are activated in the intestines in the presence of bile salts.

Bile salt-activated lipase exists in two forms. One is produced by the pancreas and is referred to as pancreatic bile salt-activated lipase or pancreatic carboxylesterase. The other is found in milk and is referred to as milk bile salt-activated lipase. Because of their functional and chemical similarities, these enzymes represent a pair of isozymes. They are directed to the same substrate, fatty acid esters, but are released independently into the digestive tract. [Wang and Kloer, Biochim. Biophys. Acta, 252:142–149 (1983)].

Milk bile salt-activated lipase has been found only in the milk of certain species, namely humans, gorillas and recently cats and dogs. [Freed, et al., Biochim. Biophys. Acta, 878:209–215 (1986)]. Milk bile salt-activated lipase is not produced by cows, horses, rats, rabbits, goats, pigs or Rhesus monkeys. [Blackberg, et al., FEBS Lett. 112:51–54 (1980); Freudenberg, Experientia 22:317 (1966)].

Although milk bile salt-activated lipase and its isozyme pancreatic carboxylesterase have been the subject of considerable study, the physiological significance of these enzymes heretofore has remained unknown. The present invention is based on the discovery that bile salt-activated lipase plays a major rate-limiting role in growth. Accordingly, the present invention is directed to supplementation of dietary compositions, such as infant formulas, with milk bile salt-activated lipase or pancreatic carboxylesterase. Also, pathological conditions involving pancreatic dysfunction, such as cystic fibrosis, may be treated by administering these enzymes to the subject in conjunction with the ingestion of fats.

In accordance with the present invention, a dietary base from a first source is selected. The composition of the base, the balance of protein, carbohydrates, vitamins, etc., will be designed to supply the nutritional needs of the subject who will consume it. Among these other ingredients, the base contains fats or triglycerides. The source of the fat also may vary according to the intended purpose of the composition and the subject involved. For example, when the composition is an infant formula, the fat usually will be milk fat.

The nutritional base of this invention is poor in bile salt-activated lipase ("BAL") in that insufficient amounts of the enzyme are present to permit optimum hydrolysis of the fats in the intestines when exposed to bile salts. Indeed, most bases will contain no bile salt-activated lipase.

An important application of the present invention is a fortified infant formula for human infants. Thus, in this embodiment the preferred nutritional base usually will comprise cow's milk, which does not contain BAL. Preferred nutritional bases for this application include commercially prepared cow's milk and commercially prepared infant formulas comprising cow's milk. Suitable formulas include those marketed under the names Enfamil ® by Mead-Johnson & Company (Evansville, Ind.) and Similac ® by Ross Laboratories (Columbus, Ohio).

It will be appreciated that in many instances the preferred nutritional base will contain no milk, such as where the composition is an infant formula for an infant who does not tolerate milk well. In such cases, preferred nutritional bases include milk-free infant formulas which usually contain soy protein. These include ProSobee ® marketed by Mead-Johnson & Company and Isomil ® marketed by Ross Laboratories.

Having selected a suitable nutritional base for the composition, bile salt-activated lipase next is prepared. Milk BAL or pancreatic carboxylesterase may be used. As will later appear, the enzyme may be purified from natural sources or it may be produced by genetic engineering. When the amino acid sequences of these enzymes or their function fragments have been identified, synthetic BAL or its active fragments may be constructed artificially. It will be understood that through these various technologies, enzymes may be produced which are functionally similar but not structurally identical.

Accordingly, as used herein, the term bile salt-activated lipase includes pancreatic carboxylesterase and milk bile salt-activated lipase as well as functionally equivalent enzymes and fragments thereof, regardless of their source or method of production. An enzyme or fragment is functionally equivalent if it is characterized by being bile salt-activated and capable of hydrolyzing fatty acid esters. Likewise, as used herein, to be derived from these enzymes or their natural sources, such as pancreatic tissue (juice) or milk, means to be produced directly, such as by purification, or indirectly by genetic engineering, protein synthesis or the like.

The BAL used in the composition preferably will be derived from the same animal species as the subject who will consume the composition. For example, where the intended subject is human, the BAL preferably will be derived from a human source, such as human milk or human pancreatic carboxylesterase. However, as indicated, milk BAL is present in the milk of at least three other animal species, namely gorillas, cats and dogs, and the studies described below demonstrate functional similarity and high species cross-reactivity between cat BAL and human BAL. Thus, it will be understood that while BAL from the same species as the subject is preferred, BAL from another species may be employed successfully.

BAL may be isolated from milk and purified for use in accordance with the present invention. A preferred method for isolating BAL from milk is described by Wang and Johnson. [Anal. Biochem. 133:457–461 (1983)]. This method utilizes affinity chromatography wherein the enzyme is collected using a cholate Sepharose support. Lactoferrin is removed using a heparin Sepharose support. Using this technique, about 30 mg of purified enzyme may be obtained from 450 ml of human skim milk. Preferably, the end product will be lyophilized. It then may be used later in the powdered state or resolubilized. If the enzyme is stored in solution, it should be kept under refrigeration.

Alternately and preferably, BAL may be produced using now well established recombinant DNA technology. This artificial production of bile salt-activated lipase will be more economical and efficient than purification processes. Several procedures are suitable. For example, the complement DNA of human BAL may be isolated and used to engineer expression vectors for synthesis of the enzyme in microorganisms, or in mammalian or other cell lines. A source of the messenger RNA of human BAL in human mammary gland cell lines, ATCC No. HBL-100, is available from American Type Culture Collection (Rockville, Md). Another source of complement DNA of human BAL is the cDNA libraries of lactating human breast tissue in λ phages (λ gt 10 and λ gt 11) which may be obtained from Clontech Laboratories, Inc. (Palo Alto, Calif.).

As naturally occurring BAL has been isolated, anti-BAL antibodies may be produced and used to find the BAL clones in the expression libraries. Alternately, a partial structure of the purified BAL could be determined and used to design nucleotide probes for finding the BAL clones.

Expression vectors and promoters for $E.$ $coli$, yeast and other microorganisms are available for synthesizing BAL. Also, expression systems, such as viral and mammalian promoters and mammalian cell lines, are commercially available for engineering BAL expression systems in other cell lines.

Transgenic animal technology offers another means for synthesizing BAL. The cloned human BAL gene first can be isolated from genomic DNA and then transferred into another animal or mammalian cell line for synthesis of the enzyme. Human genomic libraries are commercially available or may be prepared easily in most laboratories. Complement DNA for human BAL can be isolated as described above and used as a probe to find the BAL gene in the genomic libraries. The gene transfer can be accomplished by known techniques. For example, gene transfers into mice and other animals has been employed successfully by using microinjections of foreign genes into fertilized eggs.

By this transgenic technology, other animals, such as cows, can be caused to produce milk which contains human BAL. This will not only produce large amounts of the enzyme, but will produce it in a milk base. If a dietary composition of this invention is produced in this manner, it will be understood that the milk should not be subjected to heat, i.e. in excess of 50° C, as this will reduce the activity of the enzyme. In particular, methods of preparing the milk should not include conventional boiling procedures.

Pancreatic carboxylesterase may be isolated from pancreatic juice by affinity chromatography as described by Wang and Kloer. [Biochim. Biophys. Acta, 754:142–149 (1983)]. However, as with milk BAL, it is expected that synthesis, such as by recombinant DNA or transgenic technologies described above, will provide a more abundant and economical source of this enzyme.

Having obtained BAL in a substantially purified state, the BAL is added to the nutritional base. Because the preferred base is in a liquid form, i.e. milk or formula, the BAL may be added to the base in its powdered form. Alternately, the BAL may be resolubilized, such as in water or some other non-acidic solution, and then mixed with the base.

The BAL is added in an amount sufficient to improve hydrolysis of the fats in the base by the subject. Where the subject is of a species whose milk contains BAL, such as humans, the amount of BAL normally present in the milk of that species may be used as a guide. For example, it has been shown that human milk contains about 0.1 mg BAL per/ml of human skim milk. Accordingly, the preferred concentration of BAL in 1 ml of this invention would be at least about 0.001 mg, more preferably at least about 0.05 mg and most preferably about 0.1 mg. Alternately, the lipase should be present in the composition in at least a 1:2000 ratio (by weight) to the amount of fats in the composition, more preferably in a ratio of at least 1:1000, and most preferably about 1:200. That is, a preferred amount of lipase is 1 mg for every 200 mg of fat in the composition.

In accordance with the present invention, a method is provided for fortifying cow's milk. Bile salt-activated lipase, derived from an animal species other than cow, is added in an effective amount to the milk. The BAL may be obtained or prepared as described above. As indicated above, an effective amount is at least enough to improve hydrolysis of fats in the milk when the milk is digested by a subject, such as a human infant. Where the subject is human, the preferred BAL will comprise human pancreatic carboxylesterase or human milk BAL, and most preferably the latter. The preferred concentration is about 0.1 mg BAL per 1 ml milk, or about 1 mg of BAL per 200 mg of fat.

Similarly, the present invention provides a method for fortifying a fat-containing infant formula which is poor in bile salt-activated lipase. The formula preferably comprises cow's milk, but alternately may be a non-milk based formula. BAL is added to the formula in an effective amount as described previously. The BAL preferably is derived from an animal of the same species as the infant. Alternately, pancreatic carboxylesterase may be used, also preferably derived from the same species as the infant to consume it.

The present invention further includes a method for treating a subject for inadequate pancreatic production of bile salt-activated lipase, and in particular pancreatic carboxylesterase. Such conditions occur in subjects suffering from pancreatic disease or trauma resulting in reduced fat absorption. Also, genetic disorders, such as cystic fibrosis, may affect enzyme production by the pancreas, and thus, fat absorption.

The method of the present invention provides a treatment for these maladies. In accordance with this method, BAL is administered to the subject in conjunction with the ingestion of fats by the subject. The BAL may be pancreatic carboxylesterase or milk BAL and may be administered in powdered or liquid form. It may be mixed with the subject's food or drink, or may be given in an enteric coated capsule or tablet. It may be given shortly before or after the meal, or with the meal.

The BAL is administered in an amount sufficient to improve the subject's absorption or digestion of the ingested fats. It should be noted that the level of pancreatic function may vary among subjects in need of this therapy. Thus, fat absorption studies may be desirable to determine more precisely the amount of BAL required to achieve optimum fat absorption in a particular subject.

It will be understood that some of the above mentioned disorders also involve an absence or deficiency of bile salt production. In such case, successful treatment in accordance with the present invention may require concomitant administration of bile salts. When this is necessary, the bile salts and the enzyme should not be allowed to react with the fats prior to their ingestion, as this will result in unpalatable flavor.

Although it has not been confirmed, it is believed that in human infants and particularly in premature infants, pancreatic development and therefore enzyme production is incomplete at birth. The presence of BAL in human milk is thought to be a compensatory mechanism for the infant's immature pancreatic function. However, many human infants are not breast fed, and the most common infant formula comprises cow's milk which does not contain milk BAL.

Thus, the present invention provides an improved method for feeding infants. A dietary base from a first source and comprising fats is administered to the infant. The base preferably comprises cow's milk or a prepared infant formula comprising cow's milk. However, if necessary, a milk-free formula with the necessary fats may be employed.

BAL from a second source also is administered to the infant in an amount sufficient to improve the infant's digestion of fats in the formula, and most preferably at the rate of about 1 mg per 200 mg fat in the base. Preferably, the BAL is obtained from the same species as the infant, so that human BAL, preferably milk BAL, is given to human infants. The BAL may be administered with the base or shortly before or after it.

EXAMPLES

1. MILK BILE SALT-ACTIVATED LIPASE ACTIVITY STUDIES OF HUMAN AND CAT MILK

Recently Freed, et al. reported the presence of bile salt-activated lipase in the milk of cats and dogs. [Biochim. Biophys. Acta, 878:209–215 (1986)]. We performed studies to confirm this.

Cat milk was obtained from 4 common cats. The milk was expressed using a device similar to that described by McKenzie and Anderson .[J. Dairy Sci., 62:1469–1470 (1979)] for milking small animals. Samples of fifteen day post partum human milk was obtained from Oregon Health Science Center (Portland, Oreg.) and shipped in dry ice.

Samples of cat milk and human milk were tested for lipase activity using trioleoylglycerol as a substrate according to the procedure described by Wang, et al. [Clin. Chem. 27:663668 (1981)]. All assays were carried out in a $NH_4OH$-HCl buffer solution at a pH of 8.5. The substrate (trioleoylglycerol) concentration was 10 umol/ml and 0.1 uCi/mol of the labeled substrate, namely glycerol tri[$C^{14}$] oleate (from Amersham Corp. of Arlington Heights, Ill.). The concentration of bovine serum albumin was 60 mg/ml of solution, and the concentration of the activator taurocholate (bile salt) was 20 mM of solution. The final volume of the assay mixture of 1.0 ml.

After incubation of the mixture at 37° C. in a shaking water bath for 1 hour, the reaction was stopped by adding 4 ml of a mixture of isopropanol and 1.5 M $H_2SO_4$ (40:1, v/v). After mixing, the lipids were extracted by further addition of 2 ml water and 5 ml of hexane, and shaking with a votex. Fatty acids were extracted from 3 ml of the separated hexane layer with 1 ml of 0.2 M KOH. A 0.5 ml aliquot of the aqueous KOH solution was taken for measurement of the radioactivity in the usual manner on a scintillation counter. One unit of activity was defined as the amount of enzyme catalyzing the release of 1 $\mu$mol of fatty acid per hour at 37° C. The results are shown in Table 1.

TABLE I

BILE SALT-ACTIVATED LIPASE ACTIVITY IN CAT AND HUMAN MILK SAMPLES

| | Cat Milk | | | | | | Human Milk | |
| --- | --- | --- | --- | --- | --- | --- | --- | --- |
| | 3 days Postpartum | | 6 days Postpartum | | 12–18 days Postpartum | | 15 days Postpartum | |
| | u*/ml | cpm | u/ml | cpm | u/ml | cpm | u/ml | cpm |
| Sample 1 | 439 | 5869 | 341 | 5339 | 224 | 3176 | Sample 1  556 | 3521 |
| Sample 2 | 169 | 2673 | 205 | 3229 | 183 | 2465 | Sample 2  550 | 3483 |
| Sample 3 | 536 | 8377 | 281 | 4567 | 244 | 3839 | Sample 3  615 | 3888 |
| Sample 4 | — | — | — | — | 146 | 2391 | Sample 4  4199 | |
| | | | | | | | Sample 5  599 | 3791 |
| | | | | | | | Sample 6  358 | 2278 |
| Average | 381 | — | 275 | — | 199 | — | 557 | — |
| SEM | 110 | | 39 | | 122 | | 43 | |

TABLE I-continued

BILE SALT-ACTIVATED LIPASE ACTIVITY
IN CAT AND HUMAN MILK SAMPLES

| | Cat Milk | | | | | Human Milk | |
|---|---|---|---|---|---|---|---|
| | 3 days Postpartum | | 6 days Postpartum | | 12–18 days Postpartum | | 15 days Postpartum |
| | u*/ml | cpm | u/ml | cpm | u/ml | cpm | u/ml cpm |
| N | 3 | | 3 | | 4 | | 6 |

*Values expressed are units of activity. One unit is defined as the amount of enzyme catalyzing the release of 1 μmol of fatty acid per hour at 37°C.

The data in Table I confirmed previous reports on bile salt-activated lipase. It was also observed that the mean activity of this enzyme in cat milk declines with the length of the lactation period. However, this decrease is believed to be insignificant statistically because of the wide range of enzyme activity along the animals tested. Human milk contains about twice the enzyme activity as did cat milk.

2. COMPARATIVE IMMUNOCHEMICAL ACTIVITY OF CAT AND HUMAN ENZYME

The functional similarity of cat BAL and human BAL, that is that both enzymes hydrolyze fats, has been previously reported. [Freed, et al., Biochim. Biophys. Acta, 878:209–215 (1986)]. However, the immunochemical similarity of these enzymes had not been demonstrated. Accordingly, we next examined the cross-reactivity of human BAL and cat BAL by performing antibody inhibition studies.

Antibodies against human bile salt-activated lipase were prepared from a rabbit. The antibodies in the antiserum from the rabbit was collected and purified using affinity chromatography. Specifically, we used an affinity column loaded with covalently linked purified human BAL and Sepharose 4B. 3 M NaSCN was used to elute the retained antibodies. The monospecific antibodies then were used in a lipase assay procedure to test reactivity of the antibodies with human milk bile salt-activated lipase and with cat milk bile salt-activated lipase. The results are shown in Table II.

TABLE II

EFFECT OF HUMAN MILK BAL ANTIBODIES
ON BAL ACTIVITY IN HUMAN MILK,
CAT MILK AND ANTIBODY-FREE SERUM

Control
(Non-BAL immunized rabbit serum gamma globulin)

| Antibody Aliquots (ml) | % Activity Remaining | CPM* | BAL Activity ** |
|---|---|---|---|
| 0.000 | 100.0 | 2001 | 290.29 |
| 0.025 | 100.9 | 2019 | 292.90 |
| 0.050 | 99.6 | 1994 | 289.29 |
| 0.100 | 97.8 | 1957 | 283.91 |
| 0.150 | 98.0 | 1961 | 284.45 |
| 0.200 | 96.9 | 1938 | 281.15 |

Cat Milk

| Antibody Aliquots (ml) | % Activity Remaining | CPM* | BAL Activity** |
|---|---|---|---|
| 0.000 | 100.0 | 2001 | 290.29 |
| 0.025 | 87.3 | 1747 | 253.44 |
| 0.050 | 74.5 | 1491 | 216.30 |
| 0.100 | 45.4 | 908 | 131.73 |
| 0.150 | 32.9 | 659 | 95.60 |
| 0.200 | 23.7 | 475 | 68.91 |

Human Milk

| Antibody Aliquots (ml) | % Activity Remaining | CPM* | BAL Activity** |
|---|---|---|---|
| 0.000 | 100.0 | 993 | 144.06 |
| 0.025 | 41.1 | 408 | 59.19 |
| 0.050 | 15.0 | 149 | 21.62 |
| 0.100 | 5.4 | 54 | 7.83 |
| 0.150 | 5.1 | 51 | 740 |
| 0.200 | 3.0 | 30 | 4.35 |

*Value reflects correction background CPM reading which equaled 42.
**Expressed in units, one unit being defined as the ampount of enzyme catalyzing the release of 1 μmol of fatty acid per hour at 37° C.

As Table II shows, antibodies against bile salt-activated lipase from human milk inhibited enzyme activity in both cat milk and human milk. However, the human enzyme antibodies were only about 70% as reactive with the cat enzyme as with the human enzyme. From this we concluded that cat and human milk BAL are strongly cross-reactive between the species, but are not identical.

3. COMPARATIVE GROWTH STUDIES

Having verified that cat's milk contained bile salt-activated lipase and that human BAL was immunochemically similar to cat BAL, kittens were chosen as an ideal animal model to study the digestive function of this enzyme using purified human BAL. Three pregnant cats of common variety were selected and allowed to deliver their litters normally. Each litter had six kittens (two died). All of the kittens from each litter were allowed to breast feed normally for 48 hours after birth to ensure survival. At the end of this initial breast feeding period, the five-day feeding experiment was begun.

From each of the three litters, four kittens were selected arbitrarily — two males and two females. One male and one female from each litter was used as control; and similarly, one male and one female from each group were used as the study group. The rest of the kittens were allowed to continue breast feeding throughout the five-day study. However, two of the remaining six kittens died, so the breast fed group comprised four kittens.

The six kittens in the control group were fed a mixture of commercially prepared kitten formula (Borden ® Liquid KMR ® Milk Replacer for Kittens manufactured by Pet-AG, Inc. of Hampshire, Ill.) mixed three parts to one part with commercially prepared homogenized vitamin cow's milk (Borden's ® Homogenized Vitamin D milk). The six kittens in the study group were fed the same formula except that it was supplemented with purified human bile salt-activated lipase at a concentration of 0.1 mg lipase per 1 ml of formula. The lipase used was purified from human milk as described by Wang, et al. [Anal. Biochem. 133:457–461 (1983)].

Each kitten was fed manually at the rate of 2 ml formula every hour for 5 days. The formula was prepared fresh daily. Each kitten was weighed daily at about the same time, and the weights were recorded. The results are shown in Table III.

TABLE III

COMPARATIVE GROWTH STUDIES OF KITTENS

| | (wt. in gms) | (wt. gain in gms/day) | | | | | Average wt. gain per day |
|---|---|---|---|---|---|---|---|
| | Day 0 | Day 1 | Day 2 | Day 3 | Day 4 | Day 5 | |
| Breast fed group | | | | | | | |
| Kitten #1 | 114.0 | 13.3 | 7.3 | 10.8 | 7.2 | 9.1 | 9.54 |
| Kitten #2 | 110.0 | 8.3 | 11.0 | 14.3 | 8.1 | 10.8 | 10.50 |
| Kitten #3 | 114.9 | 23.1 | 14.0 | 15.0 | 14.5 | 8.5 | 15.02 |
| Kitten #4 | 125.0 | 25.1 | 15.4 | 29.0 | 13.8 | 6.7 | 18.00 |
| Avg. Daily Wt. Gain | | | | | | | 13.27 |
| SEM | | | | | | | 1.97 |
| Study Group (formula + enzyme) | | | | | | | |
| Kitten #1 | 82.5 | 13.0 | 18.6 | 7.0 | 9.2 | 8.2 | 11.20 |
| Kitten #2 | 75.6 | 14.5 | 20.9 | 3.0 | 4.3 | 2.7 | 9.08 |
| Kitten #3 | 109.9 | 22.9 | 13.9 | 11.6 | 11.4 | 5.5 | 13.06 |
| Kitten #4 | 109.6 | 15.6 | 13.6 | 10.8 | 6.6 | 6.1 | 10.54 |
| Kitten #5 | 103.4 | 14.1 | 21.3 | 4.0 | 7.1 | 12.8 | 11.86 |
| Kitten #6 | 96.1 | 19.7 | 16.0 | 6.7 | 10.5 | 9.9 | 12.56 |
| Avg.Daily Wt. Gain | | | | | | | 11.38 |
| SEM | | | | | | | 0.59 |
| Control Group (formula only) | | | | | | | |
| Kitten #1 | 100.6 | 4.7 | 9.0 | 2.5 | 1.1 | 1.4 | 3.74 |
| Kitten #2 | 95.0 | 6.8 | 2.9 | 18.6 | 7.4 | 8.9 | 8.92 |
| Kitten #3 | 115.5 | 5.2 | 5.8 | 3.1 | 3.8 | 3.8 | 4.34 |
| Kitten #4 | 114.1 | 8.3 | 3.0 | 3.6 | 5.2 | 5.8 | 5.18 |
| Kitten #5 | 101.2 | 10.9 | 14.3 | 6.6 | 6.9 | 0.1 | 7.76 |
| Kitten #6 | 106.5 | 19.6 | 6.1 | 7.4 | 5.8 | 5.3 | 8.84 |
| Avg. Daily Wt.Gain | | | | | | | 6.46 |
| SEM | | | | | | | 0.95 |

As the information in Table III shows, the kittens in the breast fed group grew at an average rate of 13.3 +/−2.0 gm/day. The kittens in the study group (those receiving formula supplemented with enzyme) grew at nearly the same rate —11.4 +/−0.6 gm/day. On the other hand, the control group (those fed with unsupplemented formula) grew at less than half that rate, 6.5 +/−1.0 gm/day. From these results we concluded that bile salt-activated lipase definitely represents the major rate-limiting factor in fat absorption and therefore growth of kittens. Having established the immunochemical similarity of human and cat BAL, we further concluded that BAL plays an equally important role in the growth of human infants.

Based on the foregoing, it will be appreciated that the present invention provides a simple, inexpensive and accessible dietary supplement to improve digestion of fats and the overall nutritional status. Among many important applications is the preferred embodiment of this invention which relates to formulas and feeding methods for human infants.

Changes may be made in the nature, composition, operation and arrangement of the various elements, steps and procedures described herein without departing from the spirit and scope of the invention as defined in the following claims.

What is claimed is:

1. A dietary composition for a human or non-ruminant animal comprising:
   a nutritional base from a first source, the base containing fats and being poor in pile salt-activated lipase selected from the group consisting of milk bile salt-activated lipase and bile salt-activated pancreatic carboxylesterase; and
   an effective amount of an isolated bile salt-activated lipase derived from a second source to increase fat absorption from the first source and growth of human or non-ruminant animal.

2. The composition of claim 1 in which the first source is selected from the group consisting of cow's milk and infant formula not containing human milk.

3. A method for fortifying a fat-containing infant formula which is poor in bile salt-activated lipase comprising adding to the formula an effective amount of an isolated bile salt-activated lipase selected from the group consisting of milk bile salt-activated lipase and bile salt-activated pancreatic carboxylesterase to increase fat absorption from the formula and growth of the infant.

4. The method of claim 3 in which the infant formula comprises cow's milk.

5. The method of claim 3 in which the formula is milk-free.

6. A method for treating a subject for inadequate pancreatic bile salt-activated lipase production, comprising:
   administering to the subject, in conjunction with the oral ingestion of fats, an isolated bile salt-activated lipase selected from the group consisting of milk bile salt-activated lipase and bile salt-activated pancreatic carboxylesterase in an amount sufficient to improve the digestion of the fats and increase absorption and metabolic utilization of the fats by the subject.

7. The method of claim 6 in which the lipase is administered with the fats.

8. The method of claim 6 in which the lipase is administered before or after the fats are ingested.

9. The method of claim 6 in which the lipase is derived from pancreatic tissue.

10. The method of claim 6 in which the lipase is derived from human pancreatic tissue.

11. The method of claim 6 in which the lipase is derived from milk.

12. The method of claim 6 in which the milk is human.

13. A method for feeding an infant a dietary base from a first source comprising fats; and administering an isolated bile salt-activated lipase selected from the group consisting of milk bile salt-activated lipase and bile salt-activated pancreatic carboxylesterase to the infant in an amount sufficient to improve the infant's digestion and absorption of the fats in the base and increase the growth of the infant, wherein the lipase is derived from a second source.

14. The method of claim 13 in which the lipase is administered with the dietary base.

15. The method of claim 13 in which the lipase is administered before or after the dietary base.

16. The method of claim 13 in which the dietary base comprises cow's milk.

17. The method of claim 13 in which the infant is human, the lipase is derived from human milk, and the dietary base comprises cow's milk.

18. The method of claim 13 in which the infant is human and the lipase is derived from human pancreatic tissue.

19. A composition for improving the absorption and metabolic utilization of ingested fats comprising:

an isolated bile salt-activated lipase selected from the group consisting of milk bile salt-activated lipase and bile salt-activated pancreatic carboxylesterase in a vehicle suitable for oral ingestion, wherein said lipase is present in a dosage providing at least 1 mg lipase/2000 mg ingested fat.

20. The composition of claim 19 wherein said lipase is present in a dosage providing approximately 1 mg lipase/200 mg ingested fat.

21. The composition of claim 19 wherein said lipase is selected from the group consisting of human milk bile salt-activated lipase, gorilla milk bile salt-activated lipase, dog milk bile salt-activated lipase, and cat milk bile salt-activated lipase.

22. The composition of claim 19 further comprising an enteric coating encapsulating said lipase.

23. The composition of claim 19 wherein said lipase is concentrated to greater than 0.1 mg lipase/ml vehicle.

* * * * *